(12) United States Patent
Lang et al.

(10) Patent No.: US 10,226,615 B2
(45) Date of Patent: Mar. 12, 2019

(54) ELECTRODE SET, IN PARTICULAR FOR A DEFIBRILLATOR

(71) Applicant: Leonh. Lang, Innsbruck (AT)

(72) Inventors: Burrhus Lang, Innsbruck (AT); Simon Foeger, Telfs (AT)

(73) Assignee: Leonh. Lang, Innsbruck (AT)

( * ) Notice: Subject to any disclaimer, the term of this patent is extended or adjusted under 35 U.S.C. 154(b) by 0 days.

(21) Appl. No.: 15/275,891

(22) Filed: Sep. 26, 2016

(65) Prior Publication Data

US 2017/0080206 A1    Mar. 23, 2017

Related U.S. Application Data

(63) Continuation of application No. PCT/AT2015/000031, filed on Feb. 23, 2015.

(30) Foreign Application Priority Data

Mar. 27, 2014 (AT) .................................. A 219/2014

(51) Int. Cl.
| | | |
|---|---|---|
| *A61N 1/00* | (2006.01) | |
| *A61N 1/04* | (2006.01) | |
| *A61B 50/30* | (2016.01) | |
| *A61N 1/08* | (2006.01) | |
| *A61N 1/372* | (2006.01) | |
| *A61B 50/31* | (2016.01) | |

(52) U.S. Cl.
CPC .............. *A61N 1/046* (2013.01); *A61B 50/30* (2016.02); *A61N 1/0476* (2013.01); *A61N 1/0492* (2013.01); *A61N 1/08* (2013.01); *A61B 2050/311* (2016.02); *A61N 2001/083* (2013.01); *A61N 2001/37294* (2013.01)

(58) Field of Classification Search
CPC ............................. A61N 1/046; A61N 1/0476
USPC ....................................................... 607/5, 142
See application file for complete search history.

(56) References Cited

U.S. PATENT DOCUMENTS

| | | |
|---|---|---|
| 4,635,642 A | 1/1987 | Cartmell et al. |
| 4,699,679 A | 10/1987 | Cartmell et al. |
| 4,827,939 A | 5/1989 | Cartmell et al. |
| 5,579,919 A | 12/1996 | Gilman et al. |
| 6,115,638 A | 9/2000 | Groenke |
| 6,743,223 B1 | 6/2004 | Lang |
| 7,822,488 B2 | 10/2010 | Jonsen et al. |
| 7,848,824 B2 | 12/2010 | Anderson et al. |
| 8,676,291 B2 | 3/2014 | Hauge et al. |

(Continued)

FOREIGN PATENT DOCUMENTS

| | | |
|---|---|---|
| DE | 10255919 A1 | 6/2004 |
| JP | S6272319 | 4/1987 |

(Continued)

*Primary Examiner* — Nadia A Mahmood

(57) ABSTRACT

An electrode set is disclosed for a defibrillator, the set including at least two electrodes each having a carrier layer, a conductive contact layer, a conductive gel layer, and a non-conductive electrode cover. In the storage state of the electrode set, the electrode covers lie against each other in a planar relationship at least portion-wise, on the side that is remote from the gel layer of the at least two electrodes. The gel layers of the electrodes are directly in contact with each other in a portion-wise manner by way of two openings in the electrode covers.

19 Claims, 3 Drawing Sheets

(56) References Cited

U.S. PATENT DOCUMENTS

Figure 1:
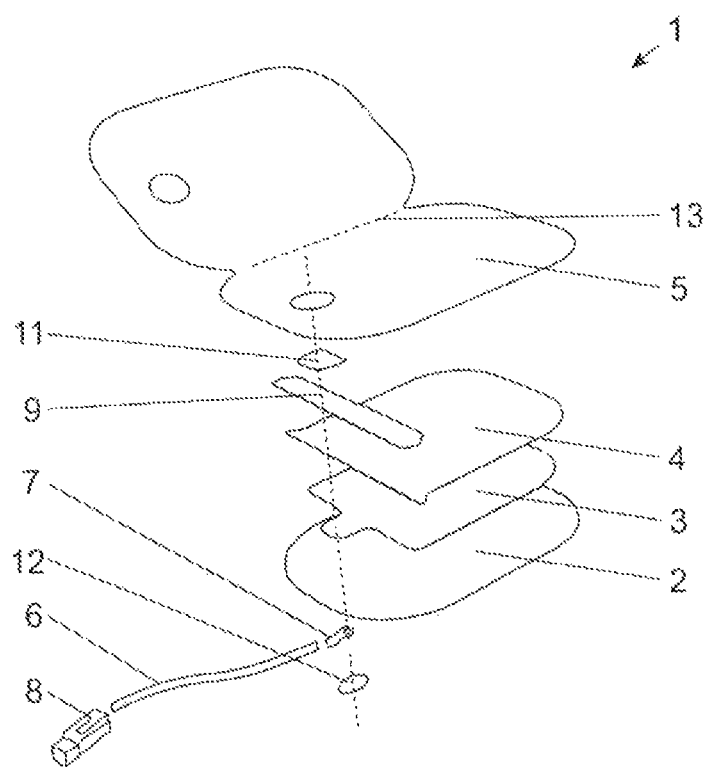

| | | |
|---|---|---|
| 8,818,529 B2 | 8/2014 | Hauge et al. |
| 2003/0055478 A1 | 3/2003 | Lyster et al. |
| 2006/0142810 A1 | 6/2006 | Denney et al. |
| 2007/0203558 A1* | 8/2007 | Jonsen .................. A61N 1/046 607/142 |
| 2008/0210592 A1 | 9/2008 | Anderson et al. |
| 2010/0094388 A1* | 4/2010 | Hauge .................... A61N 1/046 607/142 |
| 2014/0144012 A1 | 5/2014 | Hauge et al. |

FOREIGN PATENT DOCUMENTS

| | | |
|---|---|---|
| JP | 2002542865 | 12/2002 |
| JP | 2007530125 | 11/2007 |
| JP | 2008513079 | 5/2008 |
| JP | 2008272023 | 11/2008 |
| JP | 2010508939 | 3/2010 |
| WO | 2008059395 A1 | 5/2008 |

\* cited by examiner

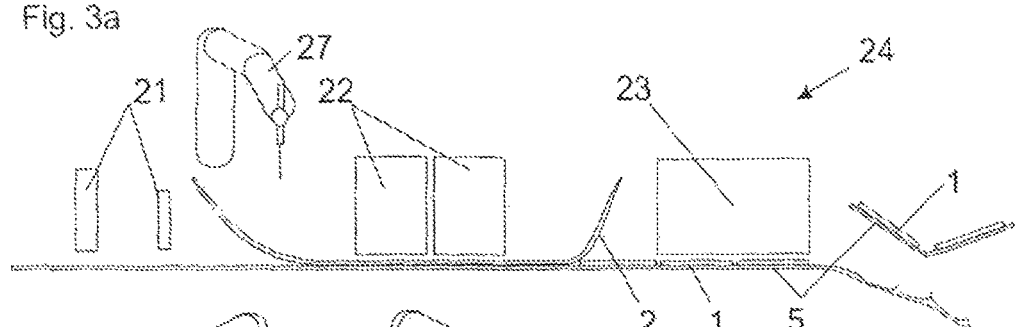
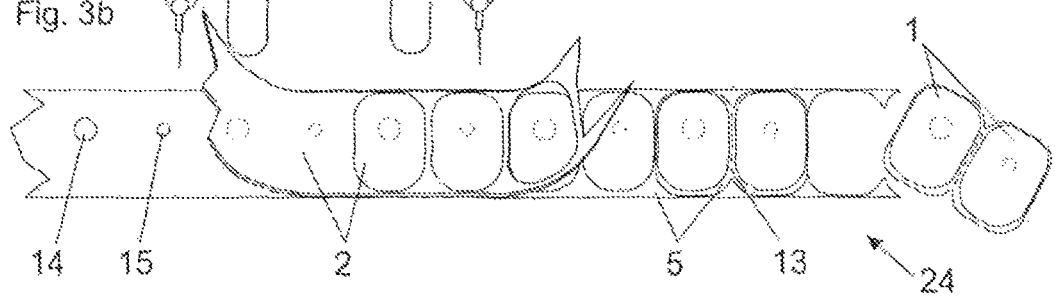
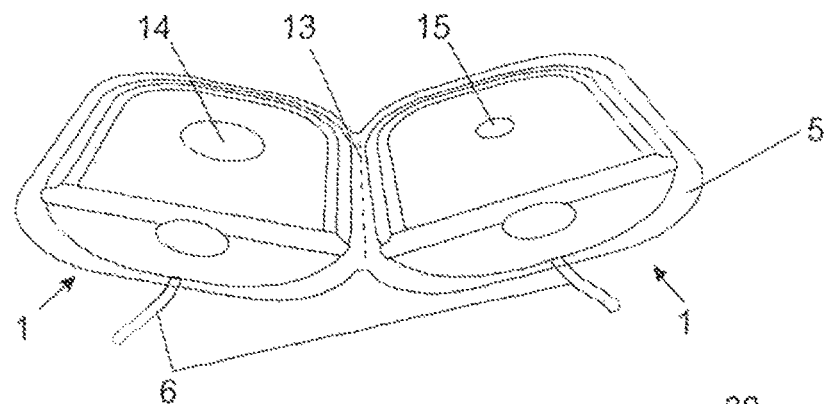
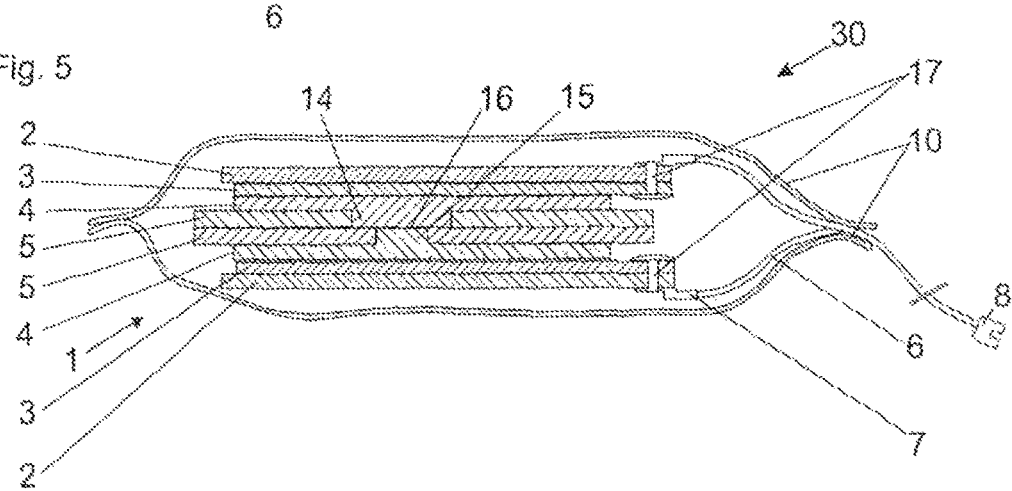

ELECTRODE SET, IN PARTICULAR FOR A DEFIBRILLATOR

PRIORITY INFORMATION

The present application is a continuation of PCT/AT2015/000031, filed Feb. 23, 2015, which claims priority to Austrian Patent Application No. A 219/2014, filed Mar. 27, 2014, the contents of which are incorporated herein by reference in their entirety.

FIELD OF THE DISCLOSURE

The present disclosure concerns an electrode set, in particular for a defibrillator, including at least two electrodes each having
- a carrier layer,
- a conductive contact layer,
- a conductive gel layer, and
- a non-conductive electrode cover.

The present disclosure further seeks to provide a process for production of the electrode set and a process for checking a conductance of a gel layer in an electrode set.

INTRODUCTION

Electrode sets of that kind are already part of the state of the art and are shown for example in U.S. Pat. No. 5,579,919.

The state of the art includes various electrode sets whose electrodes are disposed in a gas-tight packaging to protect them. The current conductors fitted to the electrodes project out of the gas-tight packaging in that case so that they can be connected to an electrical device like for example a defibrillator.

In the past, in particular for lay person defibrillators, gas-tightly packaged electrodes were used, which were able to perform so-called "inline measurement" by way of contact surfaces or additionally fitted testing contacts. That "inline measurement" serves to check the conductance of the gel layer applied on the electrode. Many electrode sets do not have additionally fitted contacts for inline measurement—in those the conductance is checked directly by way of contact surfaces shaped by the gel layer. That contact surface is produced by one or more openings in the insulating electrode cover arranged between the electrodes.

When an electrode is used it has to be removed from the packaging and fixed with the gel layer to the body of a person in question. That adhesive gel layer is at the same time also a conductor for the electric current which in an emergency situation is delivered by the defibrillator. In the event of prolonged storage it can happen that that gel layer loses its conductivity for example by drying out. That would give rise to serious problems when using the electrode. For that reason a check is periodically made by online measurement by way of the defibrillator as to whether the conductance of the gel layer is in order.

That online measurement is effected by way of a checking current which is sent from the defibrillator by way of current conductors into the packaging of the electrodes, there passes through the electrode, can flow by way of a contact surface with the other electrode and passes back to the defibrillator by way of a second current conductor. If the contact between the electrodes is not sufficiently good the defibrillator produces a warning. It will be appreciated that what is crucial for the functioning of that inline measurement is that the contact between the two electrodes occurs at the surface of the gel layer as that is intended to be checked on the basis of its conductivity.

In a specific configuration a respective electrode is applied on both sides to an electrode cover. That makes the assembly procedure complicated and expensive as in production or assembly of the electrode sets the electrode cover has to be turned during the ongoing process or the underside has to be made accessible in some other way. That results in additional working steps and higher production costs.

SUMMARY

The object of the disclosure is to avoid the above-described disadvantages and to provide an electrode set and a process for producing an electrode set, which are improved over the state of the art.

That object is attained by the features of claims 1, 20 and 24.

It has proven to be particularly advantageous in that respect if a respective separate electrode cover is provided for each electrode. The electrode covers are laid together prior to packaging and the electrodes are then disposed at the outside of the assembled electrode covers. The production costs of the electrode sets can also be reduced: as one electrode cover is provided per electrode the electrode cover does not have to be turned in the production process in order to fit it with electrodes at both sides. The electrodes which are glued on the electrode covers are packed in pair-wise relationship with each other after production.

According to a further embodiment it can be provided that the electrode covers form a common—preferably one-piece—electrode cover. The one-piece variant makes it possible for both electrodes to be fixed on one electrode cover and for same to be subsequently packaged. If both electrodes are glued on the same side—as the invention provides—it is possible to dispense with an operation of turning the electrode covers in production of the electrode set.

Fitting the electrode covers with the electrodes in production, preferably on a production belt, is effected quickly and easily from only one side—preferably from above.

If the electrode covers which are at least portion-wise substantially flat are constantly connected by way of a fold line the electrode covers can be folded together. That has the result that the folded-together electrode covers require a smaller packaging and can also be mounted to the defibrillator in space-saving relationship.

In a further embodiment it can be provided that the fold line is an at least portion-wise produced perforation in the electrode cover. Thus, when folding the electrode cover, this ensures that the electrodes lie neatly one above the other after being folded together and the cut edges and openings or positioning aids of the electrode cover are aligned with each other.

If the connected electrode covers can be folded together and are disposed between the electrodes in the storage state, this ensures that the electrodes are disposed at the outside of the unpacked electrode set. The electrodes can thus not come into contact with each other accidentally in the packaging and possibly cause errors in the inline measurement operation as contacts encounter each other.

In a further embodiment it can be provided that the overall surface area of the electrode covers is at least double the surface area of the gel layers of the electrodes and those surfaces of the electrode covers—opposite the surfaces on which the electrodes are fixed—are free from electrodes. As already mentioned that gives the effect that the electrodes cannot accidentally come into contact with each other as there is sufficient free space between the electrodes. That applies both for the one-piece variant which can be folded together and also for the "two-piece variant" with the separate electrode covers. In both variants the electrode covers are packaged in a condition of bearing against each other and the electrodes are disposed at the outsides of the electrode set. Contact of the gel layers (and the electrodes with each other) is thus excluded, except if that is wanted—for example through openings in the electrode covers.

In the region of the gel layer of each electrode there is an opening in the electrode cover. When the electrode covers are placed together the gel layers of the electrodes can form a contact with each other by touching each other, through that opening. That therefore permits inline measurement without having to fit additional contacts to the electrodes or without having to perform a complicated and expensive operation of turning the electrode cover in the production process—when using only one electrode cover with opening with fitment on both sides with an electrode.

Positioning aids like preferably guide holes or shaped portions at the outside edge of the electrode covers, which are disposed outside the receiving region of the electrodes, ensure exact positioning of the openings relative to each other in the production process when fitting the electrode covers together.

In that respect it has turned out to be particularly advantageous if the one-piece electrode cover has at least one large opening in a receiving region and at least one small opening in a further receiving region. After the electrode cover is folded together or fitted together this therefore ensures that the smaller opening always finds a place in the region of the larger opening and this ensures a clean contact surface between the two gel layers of the two electrodes. Overlapping of the openings is thus not possible by virtue of the differing sizes if the electrode cover is bent at the fold line or is folded together guided by way of the positioning aids. The openings of differing sizes give the advantage that the operation of folding the electrodes together or placing them together does not have to be implemented so precisely. That is reflected in a more efficient production speed and a lower reject rate.

If in the storage state of the electrode set the at least one small opening is aligned with the at least one large opening and as a result the gel layers of the electrodes are in contact with each other the contact surface is determined by the small opening. By connecting the gel surfaces of the two electrodes by way of the small opening in the electrode cover, that results in an electrical resistance at the small opening in the electrode cover, as soon as current flows by way of the electrodes. Thus, by way of the dimensioning of the size of the small opening, it is possible to set a fixed value for checking the conductivity of the gel layers at the electrodes. That fixed value which arises out of the size of the small opening is of the same magnitude in each packaged unit of the electrode set. In addition, in the packaged state, the difference in area between the small opening and the large opening in terms of its dimensioning represents the connecting surface of the one combination of electrode and electrode cover with respect to the other combination of electrode and electrode cover. It is advantageous that the use of an additional adhesive film or connecting agent is obviated as the adhesive property of the gel layers can be used. Thus—without using additional agents like adhesives or the like—this ensures that the two combinations of electrode and electrode cover cannot separate from each other in the packaging.

In a further embodiment it can be provided that in the storage state the at least one small opening is disposed completely in the region of the at least one large opening in order not to permit any overlaps of the two openings with each other. That is effected not only by virtue of the differing size of the openings but for example also by way of the fold line/perforation or a positioning aid. The one opening is placed over the further opening by folding at the fold line/perforation. When fitting together a "two-piece" configuration with separate electrode covers precise positioning of the openings relative to each other is effected for example by the use of positioning aids. The differing size of the openings gives additional certainty that the openings are also actually aligned with each other. That is to be expected if the area of the at least one small opening is between 30 and 70% of the area of the at least one large opening.

In a further embodiment it can be provided that the openings are preferably shaped by circles as they can be easily implemented in production and upon being folded together by way of the fold line can align with each other more easily than for example triangles or polygons.

It has proven to be particularly advantageous if at least one positioning aid is shaped by the electrode covers. Errors can be avoided when assembling the electrode sets by that positioning aid, preferably by holes or the shape of the electrode covers. This therefore prevents incorrect assembly of the electrode sets and ensures exact positioning of the openings in the electrode covers relative to each other.

In a further embodiment it can be provided that production of the openings in the material of the electrode cover is implemented prior to the adhesive electrodes being glued on the material of the electrode cover. That simplifies the stamping process and ensures that the arrangements of the openings relative to each other is always precisely stamped, as is necessary in the inline measurement procedure.

In a further embodiment it can be provided that the laser and/or the hole punch device, the electrode punch device and the card punch device are parts of an automated production installation for production of the electrode set, which permits economical production of the electrode sets.

In that respect it has proven to be particularly advantageous if an automatic feed guides the material for the electrode cover and the adhesive electrodes through the production installation. That also makes a substantially contribution to more efficient and faster production of the electrode sets.

In a further aspect of the disclosure it can be provided that a checking current, starting from an electrical device, preferably a defibrillator, is passed through the packaged electrode set which is in the storage state, wherein the at least one small opening is disposed completely in the region of the at least one large opening and thus this forms a contact surface of the electrodes relative to each other, that is defined by the area of the small opening and through which the checking current can pass through the electrode cover and the conductance value can be ascertained.

Figure 2:
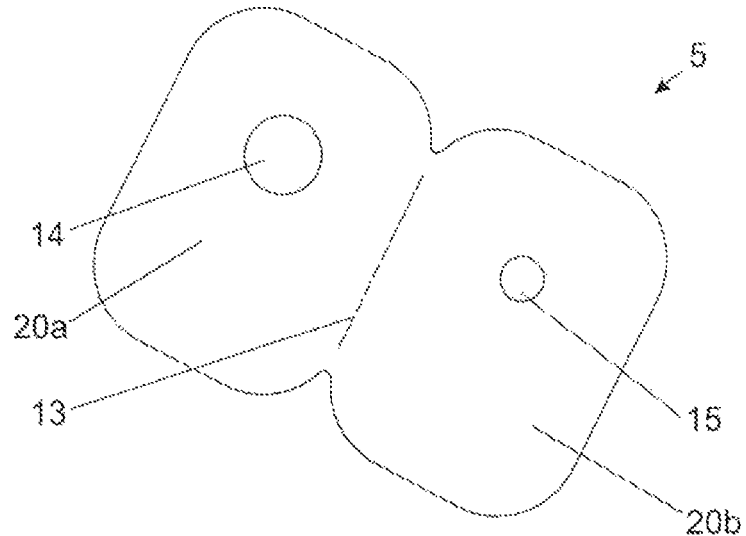
Figure 6:
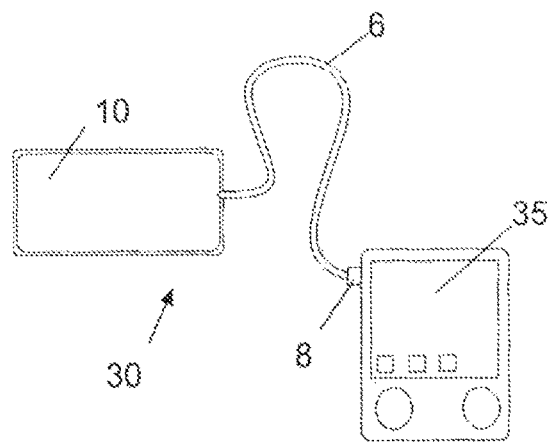
Figure 7:
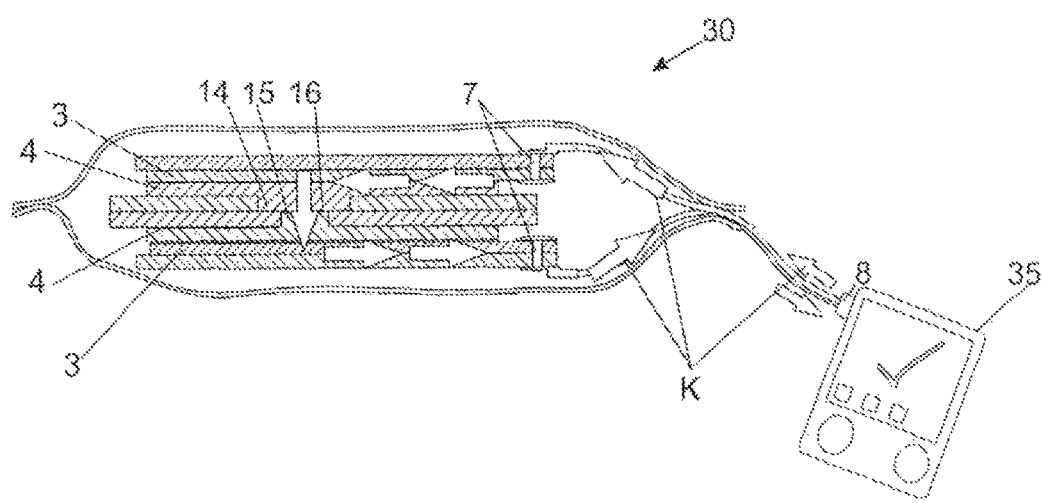
Figure 8:
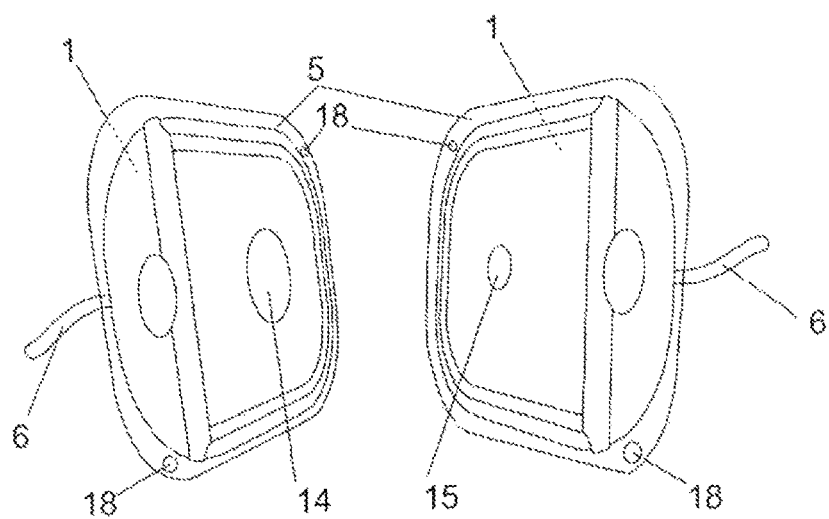

Further details and advantages of the disclosure will be described more fully hereinafter by means of the specific description with reference to the embodiments by way of example illustrated in the drawings in which:

FIG. 1 shows a diagrammatic exploded view of the constituent parts of an electrode, FIG. 2 shows a plan view of an electrode cover, FIGS. 3a and 3b show a diagrammatic view of the production procedure when stamping the electrodes on the electrode cover, FIG. 4 shows a diagrammatic view of an electrode set without packaging in the opened condition, FIG. 5 shows a diagrammatic sectional view of an electrode set in the packaged condition, FIG. 6 shows a diagrammatic view of an electrode set connected to a defibrillator, FIG. 7 shows a diagrammatic view of the current flow in the checking operation (inline measurement) of an electrode set, and FIG. 8 shows a diagrammatic view of an electrode set without packaging on individual electrode covers.

DETAILED DESCRIPTION

FIG. 1 shows an exploded view of one of electrodes which are normally arranged in pairs, comprising a carrier layer 2, preferably made from a thin foam material, a contact layer 3, preferably made from a metal film which is electrically conductive and is connected to the contact element 7. The contact element 7 is conductively fixed to a current conductor 6 having a plug 8 at its end. The gel layer 4 is disposed at the contact layer 3. The gel layer 4 comprises an adhesive, electrically conductive material and when using a defibrillator makes the connections between the body and the electrode. An adhesive element 9 is used for connecting the individual layers together. The insulating element 11 and the cover element 12 serve for insulating and covering for example a conductive rivet making the connection between the contact element 7 and the contact layer 3. The electrode cover 5 is glued by way of the gel layer 4 of the electrode 1 and protects the gel layer 4 from sticking to the second electrode which is not visible in FIG. 1.

The electrode cover 5 further has a fold line 13 which permits bending, or in other words also folding, of the electrode cover.

FIG. 2 shows an electrode cover 5 with a fold line 13 which was produced here by perforation in the form of an interrupted line. The electrode cover 5 is divided into two regions by way of the fold line 13, on the one hand into the receiving region 20a and on the other hand into the receiving region 20b. An electrode is subsequently placed on each of those receiving regions 20a, 20b. They are not yet visible in FIG. 2. A respective opening 14, 15 is disposed in each of the receiving regions 20a and 20b. The openings are so arranged that, after folding of the electrode cover 5 over the fold line 13, the opening 15 is aligned with the opening 14. If an opening 14, 15 is of larger dimensions than the other then that reduces the possibility of the openings 14, 15 not being mutually aligned after being folded together. When the electrode cover 5 is folded together for example the small opening 15 can find place in the large opening 14 and can be completely accommodated thereby. If the electrode cover were of a two-part configuration (see FIG. 8) then two openings 14, 15 of differing sizes would also simplify the assembly process—a lower degree of precision is necessary when folding them together or fitting them together. Thus the assembly process can be quicker and more advantageous.

FIG. 3a diagrammatically shows the production process for the electrode 1. In a production step the two openings 14, 15 are stamped out of a material traveling as a web for the electrode covers with the hole stamping punches 21.

In a further working step in a web the prepared electrode 1 is glued on to the material of the electrode cover. In a next working step one or more electrodes 1 are stamped, cut or lasered out of the material for the electrodes by means of an electrode stamping punch 21 either in succession or at the same time. In a further working step the remaining film, that is no longer necessary, of the carrier layer 2 of the electrode 1 is pulled off. The electrodes 1 are still disposed with their gel layer 4 placed correctly over the openings 14, 15 on the material for the electrode cover 5.

In a further working step a pair of electrodes is cut out of the material of the electrode covers by way of the card punch 23 or a laser 27. The remaining material of the film for the electrode covers 5 is removed in the next working step. Perforation of the fold line 13 in the electrode cover 5 can be produced by laser or can be effected in one working step with stamping by the card punch 23 or also subsequently in a further step.

FIG. 3b shows the same working steps as FIG. 3a as a plan view. The openings 14, 15 are only still shown in broken line after application of the carrier layer 2 for the electrodes, as the openings would otherwise no longer be visible in the diagrammatic view. In this view perforation of the fold line 13 is effected at the same time with stamping by the card punch 23 or can be cut by means of a laser 27 in the same way as the outlines of the electrode covers 5.

FIG. 4 shows an unpackaged electrode set 30 on an electrode cover 5. The electrode cover 5 which is here shown transparently is the uppermost layer in this diagrammatic view. The adhesive electrodes are stuck to the underside of the electrode cover 5. In this unfolded condition of the electrode cover 5 the small opening 15 is not in contact with the large opening 14. As soon as the electrode cover 5 is folded together by way of the fold line 13, here shown as a broken-line perforation, the gel layers 4 of the electrodes are joined to each other by way of the small opening 15.

FIG. 5 shows a diagrammatic sectional view of a packaged electrode set 30. In this case the packaging 10 encloses the complete unit consisting of the electrodes 1 and the electrode cover 5. In this case the current conductor 6 is passed gas-tightly out of the packaging. The current conductor 6 is connected to the contact layer 3 by way of connecting elements 17. The current conductor 6 which is passed out of the gas-tight packaging 10 has a plug 8 at one end. The electrode set 30 can be connected to a defibrillator 35 with that plug. The electrode cover 5 is disposed in the folded-together condition between the two electrodes 1, which is indicated here by two layers. An opening 14, 15 is provided in each of those layers consisting of the electrode cover. The gel layers 4 of the electrodes 1 are in contact with each other by way of those openings 14, 15. The contact area which is thus produced between the gel layers 4, in other words also referred to as the checking contact 16, represents the sole connection between the two gel layers 4 of the packaged electrodes 1.

FIG. 6 shows an electrode set 30 in the connected condition to a defibrillator 35 by way of a current conductor 6 and a plug 8. In this condition a checking current can be delivered from the defibrillator 35 to the electrode set 30 and received again. If there were a problem with the conductivity of the gel layer of the packaged electrodes 1 the defibrillator 35 would produce an error warning.

FIG. 7 diagrammatically shows the configuration of the checking current K starting from the defibrillator 35 through the plug 8 into the current conductor 6, preferably a two-pole cable, into the electrode set 30. In the electrode set 30 the current K flows by way of the contact element 7 into the contact layer 3 connected to the gel layer 4. The checking contact 16 formed by the openings 14, 15 allows the checking current K, shown as an arrow, to flow from the one gel layer 4 into the other gel layer 4. Subsequently the checking current K follows its further path back to the connecting element 7 and into the two-pole cable connected to the defibrillator 35 by way of the plug 8. If the checking current K can flow through the electrode set 30 without major resistance, in other words: if the inline measurement operation were successful, the electrode set 30 can continue to be used and does not have to be replaced. If the conductivity of the gel layer 4 is no longer sufficient, which could happen as a consequence of mechanical damage to the packaging or the entire electrode set 30, that is registered as a fault at the defibrillator 35. In that case the electrode set 30 has to be replaced.

FIG. 8 shows an unpackaged electrode set 30 with a respective electrode 1 on a respective electrode cover 5. In this embodiment the electrode covers are not of a one-piece structure. The electrode covers 5 which are shown here as transparent are disposed as diagrammatically illustrated in front of the electrodes 1 and conceal the electrodes 1. In this condition of the electrode covers 5, in which they are not folded together, the small opening 15 is not in contact with the large opening 14. As soon as the electrode covers 5 are placed together at their sides remote from the electrodes the electrodes 1 come into communication with each other by way of the small opening 15. What is important in that respect is that, when the electrode covers 5 are placed together, care is taken to ensure that the openings 14, 15 are aligned, or the small opening 15 is actually disposed in the larger opening 14. That can be effected for example by way of positioning aids 18 arranged in the electrode covers 5. Thus for example a device can receive the electrode covers 5 at the positioning aids 18 and connect them together in the correct position. The positioning aids 18 can also be afforded by virtue of the outside shape of the electrode cover 5 and does not have to be in the form of an opening.

The invention claimed is:

1. An electrode set, in particular for a defibrillator, comprising at least two electrodes, each comprising
   a carrier layer;
   a conductive contact layer;
   a conductive gel layer; and
   a non-conductive electrode cover, wherein, in the storage state of the electrode set, the electrode covers lie against each other in planar relationship at least portion-wise, on the side that is remote from the gel layer of the at least two electrodes, wherein the gel layers of the electrodes are directly in contact with each other in portion-wise manner by way of at least two openings in the electrode covers.

2. An electrode set as set forth in claim 1, wherein the number is limited to two electrodes per electrode set.

3. An electrode set as set forth in claim 1, wherein, in the storage state of the electrode set, a current conductor is fixed to the electrodes.

4. An electrode set as set forth in claim 1, wherein, in the storage state of the electrode set, a gas-tight packaging encloses the electrode set.

5. An electrode set as set forth in claim 4, wherein, in the storage state of the electrode set, the current conductor is passed out of the gas-tight packaging.

6. An electrode set as set forth in claim 1, wherein a respective separate electrode cover is provided for each electrode.

7. An electrode set as set forth in claim 1, wherein the electrode covers form a common, one-piece electrode cover.

8. An electrode set as set forth in claim 7, wherein the electrode covers which are at least portion-wise substantially flat are constantly connected to each other by way of a fold line.

9. An electrode set as set forth in claim 8, wherein a fold line for connecting the electrode covers is provided by a perforation which is produced at least portion-wise.

10. An electrode set as set forth in claim 7, wherein the connected electrode covers are folded together and are disposed in the storage state between the electrodes.

11. An electrode set as set forth claim 1, wherein the overall surface area of the electrode covers is at least double the area of the gel layers of the electrodes.

12. An electrode set as set forth in claim 1, wherein those surfaces of the electrode covers in opposite relationship to the surfaces on which the electrodes are fixed are free of electrodes.

13. An electrode set as set forth in claim 1, wherein the electrode covers have at least one respective opening in a receiving region.

14. An electrode set as set forth in claim 13, wherein the electrode covers have at least one large opening in a receiving region and at least one small opening in a further receiving region.

15. An electrode set as set forth in claim 14, wherein, in the storage state of the electrode set, the at least one small opening aligns with the at least one large opening.

16. An electrode set as set forth in claim 14, wherein, in the storage state the at least one small opening is disposed completely in the region of the at least one large opening when the electrode cover is folded along the fold line.

17. An electrode set as set forth in claim 14, wherein the area of the at least one small opening is between 30% and 70% of the area of the at least one large opening.

18. An electrode set as set forth in claim 13, wherein the openings are formed by circles.

19. An electrode set as set forth in claim 1, wherein at least one positioning aid and/or fold line is shaped out by the electrode covers.

* * * * *